United States Patent [19]

Moden et al.

[11] Patent Number: 4,710,174

[45] Date of Patent: Dec. 1, 1987

[54] IMPLANTABLE INFUSION PORT

[75] Inventors: James R. Moden, Bristol; Michael D. Caldwell, East Greenwich; Robert D. Moden, Barrington, all of R.I.

[73] Assignee: Surgical Engineering Associates, Inc., Bristol, R.I.

[21] Appl. No.: 809,773

[22] Filed: Dec. 16, 1985

[51] Int. Cl.$^4$ ........................................... A61M 25/00
[52] U.S. Cl. ....................................... 604/175; 604/244
[58] Field of Search ................... 604/175, 244, 93, 891

[56] References Cited

U.S. PATENT DOCUMENTS

| | | | |
|---|---|---|---|
| 3,310,051 | 3/1967 | Schulte | 604/175 |
| 3,640,269 | 2/1972 | Delgado | 604/175 X |
| 4,405,305 | 9/1983 | Stephen et al. | 604/175 X |
| 4,543,088 | 9/1985 | Bootman et al. | 604/175 X |

FOREIGN PATENT DOCUMENTS

| | | | |
|---|---|---|---|
| 0134745 | 3/1985 | European Pat. Off. | 604/175 |
| 0207151 | 2/1984 | German Democratic Rep. | 604/175 |

*Primary Examiner*—Stephen C. Pellegrino

*Attorney, Agent, or Firm*—Salter & Michaelson

[57] ABSTRACT

An implantable infusion port for dispensing medication in the body of a patient comprises a septum which is preferably integrally molded from a nontoxic, rubberized material and has an interior cavity formed therein for receiving medication in the septum, and a catheter element which extends from the cavity to the exterior of the septum for dispensing medication in the body of a patient. The septum has a rounded dome-shaped configuration, and the infusion port is surgically implantable in the body of a patient so that it is positioned beneath the skin and subcutaneous tissue of the patient. After the infusion port has been implanted in the patient, medication can be introduced into the cavity by inserting a hypodermic needle through the skin of the patient and through the side wall of the septum. The rounded dome-shaped configuration and the integrally molded construction of the septum minimize patient discomfort and provide an increased needle penetration area in the infusion port so that it does not become rapidly damaged by needle penetrations and it can be effectively used over a prolonged period of time without requiring replacement.

8 Claims, 11 Drawing Figures

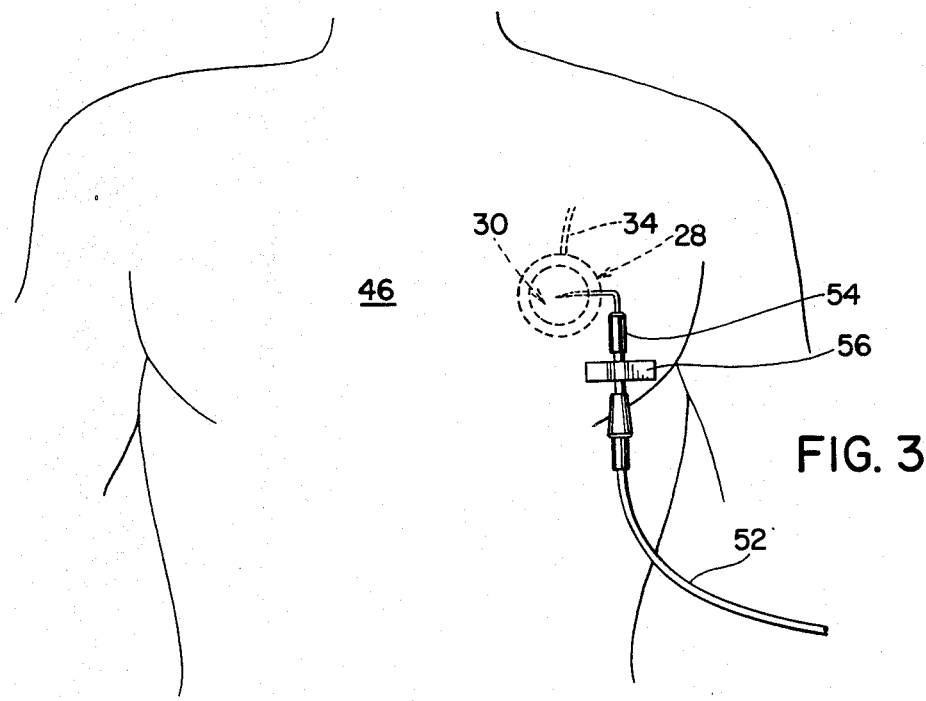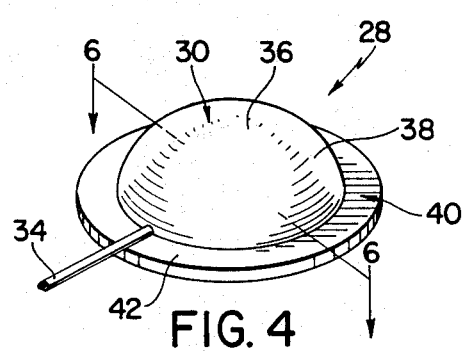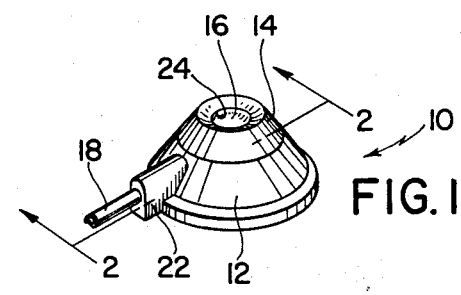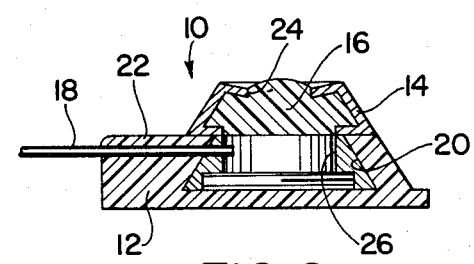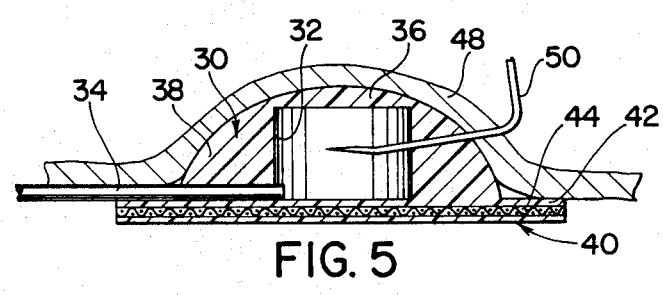

IMPLANTABLE INFUSION PORT

BACKGROUND AND SUMMARY OF THE INVENTION

The instant invention relates to medical devices which are implantable in the human body and more particularly to an implantable infusion port for dispensing medication in the body of a patient.

Infusion ports which are implantable in the bodies of patients for dispensing medications therein have been heretofore available and have been favorably accepted by the medical field for a number of years. In this connection, it has been found that implantable infusion ports can be effectively utilized for dispensing medications in the bodies of patients and that they are substantially more effective than catheters and the like for use over prolonged periods of time since they do not require permanent openings in the skin. The most common type of heretofore-available infusion port comprises a rubberized base portion, a metallic housing portion which is received on the base portion and has an open cavity formed therein which is accessible through a reduced entry passage in the upper end of the housing portion, a penetrable seal portion which is received in the entry passage in the housing portion, and a catheter element which extends from the open cavity to the exterior of the device. The housing portion is received in assembled relation with the base portion so that it cooperates therewith to define a truncated conical configuration in the infusion port and so that the entry passage is located in the upper end of the infusion port. Normally, a device of this type is surgically implanted in a patient so that it is positioned beneath the skin and so that the upper end of the housing portion and the penetrable seal face outwardly, and the catheter element of an infusion port of this type is normally installed so that it can transmit fluids from the cavity to a predetermined area of the patient's body, such as a large vein. Once an infusion port of this type has been installed in a patient, the cavity can be periodically filled with medication by inserting a hypodermic needle in the patient so that it penetrates the skin and passes through the penetrable seal portion of the device for injecting medication into the interior cavity therein. It has been found that an infusion port of this general type can be effectively utilized for dispensing medication in the body of a patient over a prolonged period of time and that it is generally preferable to a catheter or the like which would require a permanent opening in the skin, since it is substantially less likely to provide a sight for infection.

While the heretofore-available infusion ports have generally been found to be more effective than catheters and the like for introducing medications into the bodies of patients over prolonged periods of time, they have nevertheless had substantial disadvantages. Specifically, it has been found that because of the truncated conical configurations of most of the heretofore-available infusion ports, they have generally had cavities of relatively small dimension. Further, it has been found that when an infusion port includes a metallic housing having a reduced entry passage, it is sometimes difficult to locate the entry passage with the tip of a hypodermic needle when the infusion port is covered by the skin of the patient. In addition, it has been found that when the open cavity of an infusion port is defined by a metallic housing, it is possible for a hypodermic needle which is inserted into the housing to strike a wall of the housing and be damaged so that a barb is formed on the tip of the needle. When the needle is thereafter withdrawn from the infusion port, the barbed tip can cause damage to the penetrable seal portion of the infusion port, and it can also cause substantial trauma to the skin and tissue of the patient as it is withdrawn. Further, it has been found that even when a hypodermic needle is carefully inserted into an infusion port of this type so that a barb is not formed on the end of the needle, a certain amount of damage is caused to the seal portion of the infusion port; and since the entry passage has a relatively small penetration area, the relatively small seal portion can become severely damaged from needle penetrations in a relatively short period of time. Similarly, it has been found that since the entry passage of an infusion port of this type is relatively small, the needle injections which are periodically required to replenish the supply of medication in the cavity must be made through a very localized area of the patient's skin so that the skin in this area never has a chance to heal properly, and the same localized area of skin is repeatedly traumatized from adhesive tapes and antibacterial agents. In addition, it has been found that when a needle injection is made in a patient in order to introduce medication into an infusion port of this type, the needle must be positioned in substantially perpendicular relation to the skin so that bulky padded dressings are often required to provide support for the needle as the medication is introduced. Still further, it has been found that when an infusion port is made in a truncated conical configuration, it can produce an unattractive mound on the body of a patient which is likely to cause irritation when it is rubbed by clothing or when the mound is accidentally bumped or bruised; and the trauma which is caused by an accidental blow to the mound is greatly increased when an infusion port includes a metallic housing portion. In addition, it has been found that when an infusion port includes a metallic housing portion, fluoroscopic or X-ray examination of a hypodermic needle which is inserted into the infusion port is hampered by the housing portion, and that bodily fluids can migrate into seams and/or crevices in an infusion port of this type.

The instant invention provides an effective infusion port which overcomes the disadvantages of the heretofore-available infusion ports and which is operable with substantially increased effectiveness and substantially reduced patient trauma. The infusion port of the instant invention generally comprises a septum having a base portion, a side wall portion and a top wall portion which cooperate to define an enclosed cavity for receiving medication in the septum, and a catheter element which extends between the cavity and the exterior of the septum for dispensing medication in the body of a patient. At least a portion of the side wall portion of the septum is made of a material which is penetrable by a hypodermic needle for introducing medication into the cavity but which is substantially self-sealing upon removal of the needle therefrom. In the preferred embodiment, the septum is integrally formed from a non-toxic rubberized material, such as a silicone rubber, which is penetrable by a hypodermic needle but self-sealing upon removal of the needle, and the side wall and top wall portions of the septum are formed in a rounded dome-shaped configuration. The base portion is preferably formed so that it extends outwardly a distance around the periphery of the side wall portion to define a peripheral rim on the septum, and reinforcing means is preferably embedded in the rim to allow the infusion port to be secured in the body of a patient with sutures or the like. In one embodiment of the infusion port, a plurality of needle shields are embedded in the top wall, side wall, and base portions of the septum for guiding the tip of a hypodermic needle which is inserted through the side wall portion so that it passes into the cavity in the interior of the septum. In still another embodiment of the infusion port, a partition is provided in the septum for separating the cavity into first and second cavity sections or chambers, and first and second catheter elements are provided which extend between the first and second chambers and the exterior of the septum so that this embodiment of the infusion port can be utilized for administering two different medications in the body of a patient over a prolonged period of time.

Accordingly, it is seen that the infusion port of the instant invention has significant advantages over the heretofore-available infusion ports. Specifically, the septum of the infusion port of the instant invention has a substantially increased penetration area since it is adapted for side entry so that the cumulative effects of damage to the septum caused by needle penetrations are substantially reduced. Similarly, since the septum has an enlarged penetration area, the penetration area on the skin of a patient is similarly increased so that the same localized area of the skin does not have to be penetrated each time a needle injection is made. In addition, since the infusion port of the instant invention is adapted to receive hypodermic needles through the side wall portion of the septum, a needle which has been inserted into the septum can be laid flat on the skin so that it does not need to be supported by bulky dressings and the like. In addition, because of the rounded dome-shaped configuration of the septum, the infusion port of the instant invention produces a substantially less offensive mound or raised area on the body of a patient in which it is installed; and because the infusion port is preferably integrally molded of a rubberized material, trauma to the patient is substantially reduced when the area adjacent the infusion port is accidentally bumped or bruised. Still further, because of the flexibility of the infusion port, when external forces are applied thereto they are more gently distributed to underlying and overlying tissue, and therefore less trauma is caused to the patient than would otherwise be caused by a conventional infusion port. Still further, since the infusion port of the instant invention does not include a metallic housing, hypodermic needles which have been inserted into the septum cannot become barbed and they can be effectively viewed through the use of X-ray and/or fluoroscopic equipment. Still further, since the septum of the infusion port preferably has a dome-shaped configuration and the cavity preferably has a cylindrical configuration, the side wall portions of the septum have increased thicknesses and this tends to stabilize a needle which has been inserted therethrough so that the needle can be left in the patient for a prolonged period of time if needed without causing severe trauma to the overlying subcutaneous tissue. Still further, since the infusion port of the instant invention is preferably integrally molded of a nontoxic rubberized material, it does not have crevices or seams into which bodily fluids could migrate.

Accordingly, it is a primary object of the instant invention to provide an improved infusion port for administering medication to a patient.

Another object of the instant invention is to provide a side-entry infusion port for administering medication to a patient.

An even further object of the instant invention is to provide an effective infusion port which is integrally molded of a nontoxic, rubberized material.

A still further object of the instant invention is to provide an infusion port having an increased entry area.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a perspective view of the infusion port of the prior art;

FIG. 2 is a sectional view taken along line 2—2 in FIG. 1;

FIG. 3 is a view of a first embodiment of the infusion port of the instant invention installed in a patient and having a needle inserted into the infusion port;

FIG. 4 is a perspective view of the infusion port of the instant invention;

FIG. 5 is a sectional view of the infusion port of the instant invention installed in a patient and having a needle inserted into the infusion port;

DESCRIPTION OF THE INVENTION

Figure 6:
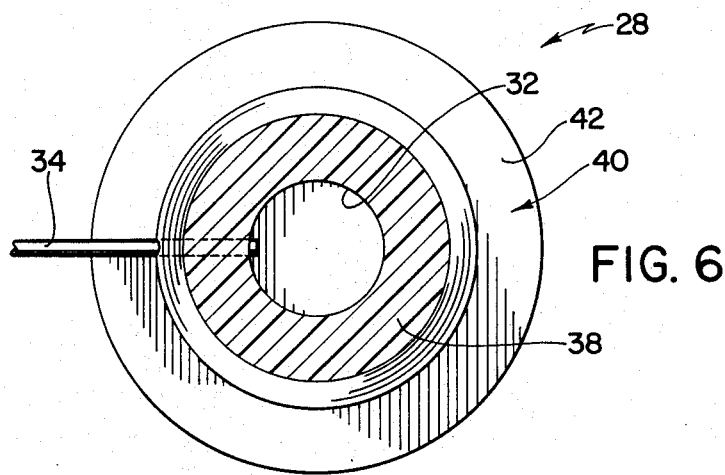
FIG. 6 is a sectional view taken along line 6—6 in FIG. 5.

Referring now to the drawings, an infusion port of the prior art is illustrated in FIGS. 1 and 2 and generally indicated at 10. The infusion port 10 is of generally truncated conical configuration, and it comprises a body portion 12, a housing portion 14, a seal element 16, and a catheter element 18. The body portion 12 is constructed of a flexible rubberized material and it has a cavity 20 formed therein, and a catheter support section 22 is integrally formed in the body portion 12. The housing portion 14 is constructed of a corrosion-resistant metal, and it has a reduced, upwardly facing entry passage 24 formed therein. The seal element 16 is constructed of a rubberized material which is easily penetrable by a hypodermic needle or the like, and it is received in the housing portion 14 so that it provides a penetrable seal for the passage 24; and accordingly, the housing portion 14 and the seal element 16 cooperate to define an open cavity 26 in the infusion port 10 for receiving and containing a medication. The catheter element 18 extends through the catheter support 22 of the body portion 12 and through the housing portion 14 so that it extends into the cavity 26 for providing communication between the cavity 26 and the exterior of the infusion port 10 for dispensing medication from the cavity 26 in the body of a patient.

During use and operation of the infusion port 10, it is surgically implanted in a patient so that it is covered by the skin and the subcutaneous tissue of the patient. In order to introduce a medication into the infusion port 10, a hypodermic needle or the like is inserted into the patient so that the tip of the needle passes through the seal element 16 and into the cavity 26. However, due to the relatively small dimension of the passage 24, the seal element 16 and the same localized area of the skin and tissue of the patient must be penetrated each time a medication is introduced into the cavity 26. Accordingly, the seal element 16 can become damaged to a significant extent in a relatively short period of time and the skin and the subcutaneous tissue of the patient in the area of the passage 24 never have a chance to completely heal. Further, because the housing 14 is of metallic construction, it can cause barbing on the tip of a hypodermic needle if the tip strikes a wall of the housing 14, so that when the needle is withdrawn from the infusion port 10, it can cause increased trauma to the patient. Still further, because of the truncated conical configuration of the infusion port 10 and the metallic construction of the housing 14, the infusion port 10 can cause substantial discomfort to a patient, particularly if the area of the patient adjacent the infusion port is accidentally bumped or bruised. In addition, because of the truncated conical configuration of the infusion port 10, it can cause a relatively unattractive mound on the body of a patient, and the cavity 26 is inherently of relatively small dimension. Still further, because medication can only be introduced into the cavity 26 through the passage 24, a needle or the like must be inserted into the infusion port 10 in substantially perpendicular relation to the skin so that often the needle cannot be effectively supported by the adjacent area of tissue or skin of the patient; and because the infusion port 10 is made in a multi-piece construction, bodily fluids can migrate between the various elements, such as the body portion 12 and the housing 14.

A first embodiment of the infusion port of the instant invention is illustrated in FIGS. 3 through 6 and generally indicated at 28. The infusion port 28 comprises a septum generally indicated at 30 which is integrally molded of a nontoxic rubberized material, such as silicone, and which has an open cavity 32 formed therein, and a catheter element 34 which is sealingly received in the septum 30 so that it extends from the cavity 32 to the exterior of the infusion port 28 for transmitting a medication from the cavity 32 to a desired area in the body of a patient. The septum 30 comprises a top wall portion 36, a side wall portion 38, and a base portion 40 which cooperate to define the interior cavity 32; and the top wall portion 36 and the side wall portion 38 are preferably formed in a rounded, dome-shaped configuration. The base portion 40 is preferably of generally planar configuration, and it preferably projects outwardly from around the periphery of the side wall portion 38 to define a peripheral rim 42 on the septum 30. Further, the base portion 40 preferably has a reinforcing layer 44 which is made of a reinforcing sheet material, such as nylon fabric or the like, embedded therein to enable to septum 30 to be effectively secured to tissue in the body of a patient by passing sutures through the rim 42. The cavity 32 which is formed in the septum 30 is preferably of right cylindrical configuration, and the septum 30 is preferably formed so that the side wall portions 38 thereof have substantial thicknesses as illustrated most clearly in FIG. 5. The catheter element 30 is preferably embedded in the septum 30 as the septum 30 is molded, and it comprises a tubular, flexible catheter element which is of a suitable length for transmitting medication from the septum 30 to a desired area of the body.

The use of the infusion port 28 is illustrated in FIGS. 3 and 5. As will be seen, the infusion port 28 is adapted to be surgically implanted in a patient, such as the patient 46, so that the infusion port 28 is covered by the skin and subcutaneous tissue 48 of the patient 46, and so that the catheter element 34 extends to a desired area, such as a large vein of the patient 46, for transmitting a medication from the cavity 32 to the vein. In order to fill the cavity 32 of the septum 30 after the infusion port 28 has been implanted in the patient 46, a needle 50 is inserted through the skin and subcutaneous tissue 48 so that it passes through the side wall portion 38 of the septum 30 and into the cavity 32. The needle 50 is preferably of the type which has a substantially right-angle bend therein as illustrated, and it is connected to a tubing 52 through a fitting assembly 54 for supplying medication to the infusion port 28. Further, because the infusion port 28 is adapted for side entry, the needle 50 is positionable adjacent the surface of the body of the patient 46 and the fitting assembly 54 is also positionable adjacent the surface of the body of the patient 46 to allow the fitting assembly 54 and the tubing 52 to be supported with an adhesive tape 56. Accordingly, medication can be introduced into the cavity 32 through the needle 50 without providing additional external supports for the fitting assembly 54. Further, since the needle 50 can be inserted through any part of the side wall portion 38, there is a relatively large penetration area in the skin 48 of the patient 46, and the penetration area of the septum 30 is also relatively large. Further, because the septum 30 is made in an integrally molded rubberized construction, the infusion port 28 is substantially less prone to causing discomfort to the patient 46, and the septum 30 does not have cracks or crevices wherein bodily fluids could migrate. Still further, because of the rounded, dome-shaped configuration of the septum 30, when the infusion port 28 is implanted in a patient, it produces a mound or raised area on the patient which is inherently less offensive than the type of mound which would be produced with the device 10, and the rounded dome-shaped configuration of the device 28 also tends to distribute external forces which are applied thereto so that patient discomfort is minimized.

Figure 7:
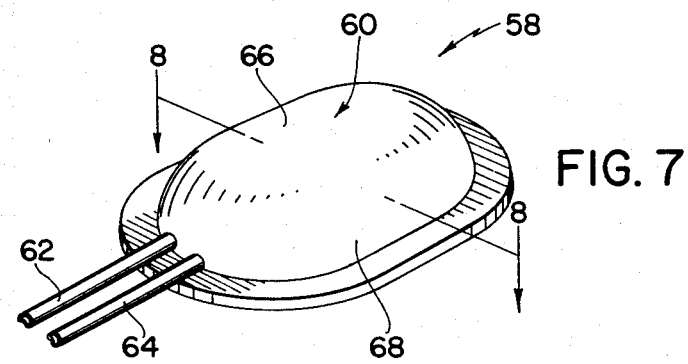
FIG. 7 is a perspective view of a second embodiment of the infusion port of the instant invention.
Figure 8:
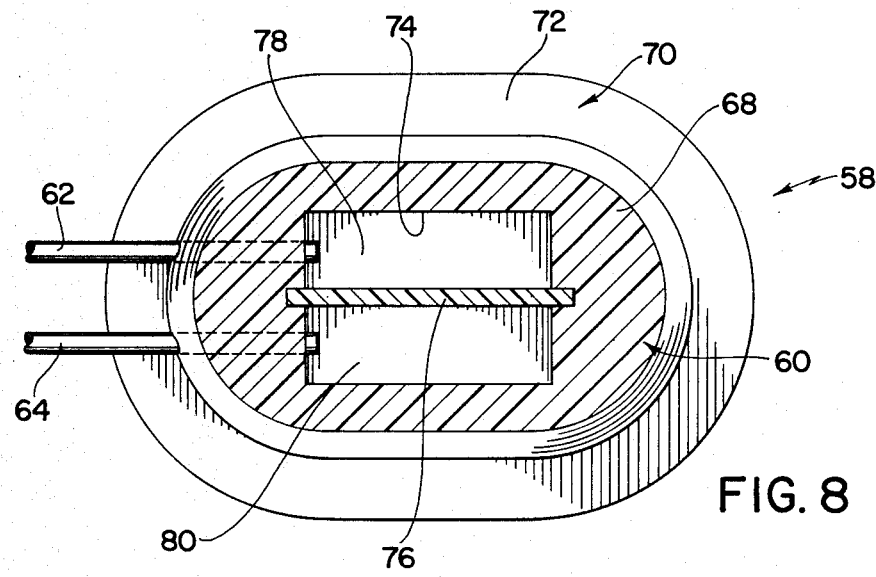
FIG. 8 is a sectional view taken along line 8—8 in FIG. 7.

Referring now to FIGS. 7 and 8, a second embodiment of the infusion port of the instant invention is illustrated and generally indicated at 58. The infusion port 58 is generally similar to the infusion port 28, although it is adapted for dispensing two different medications in the body of a patient. The infusion port 58 is of elongated form and it comprises a septum generally indicated at 60 which is also preferably integrally molded of a suitable nontoxic rubberized material, such as a silicone rubber, and first and second catheter elements 62 and 64. The septum 60 comprises a top wall portion 66, a side wall portion 68, and a base portion 70 having a peripheral rim 72. The septum 60 is of generally oval-shaped configuration, and the top wall portion 66 and the side wall portion 68 cooperate to define a rounded, oval dome-shaped element on the base portion 70; and further, the top wall portion 66, and the side wall portion 68, cooperate with the base portion 70 to define an enclosed cavity 74 in the septum 60. Provided in the interior of the septum 60, is a substantially upright impenetrable partition 76 which is preferably made of a hardened material, such as a corrosion-resistant metal, and which is preferably imperforate and disposed so that it extends in a lengthwise direction and divides the cavity 74 into first and second chambers 78 and 80, respectively elongated exterior sides which are penetrable by a needle. The first and second catheter elements 62 and 64 extend inwardly through the side wall portion 68 to so that the lumens thereof communicate with the first and second chambers 78 and 80, respectively, and they are preferably embedded in the septum 60 during the molding of the infusion port 58.

Accordingly, for use and operation of the infusion port 58, it is surgically implanted in a patient in the manner hereinabove described with regard to the infusion port 28; although, the first and second catheter elements 62 and 64 must be individually connected to appropriate areas in the body of the patient for transmitting medications thereto from the chambers 78 and 80. In order to fill the cavity 74 with medications, the chambers 78 and 80 must be individually filled by inserting needles through the appropriate adjacent areas of the side wall portion 68 so that the medications are introduced into the appropriate chambers 78 and 80. Thereafter, the medications are effectively dispensed in the body of the patient through the catheter elements 62 and 64 in the normal manner. Further, since the infusion port 58 is generally similar in construction to the infusion port 28, it has generally the same advantages in its operation and construction as the infusion port 28. As will be seen, due to the elongated form of the port 82 and the cavity 102, the side wall portion 96 defines two opposed side entry areas which are each penetrable by a needle and bounded at the ends thereof by the respective adjacent shields 92

Figure 9:
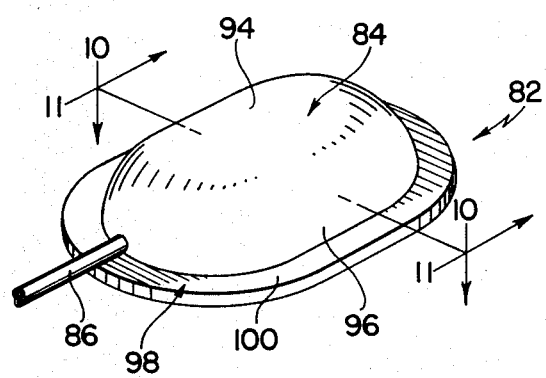
FIG. 9 is a perspective view of a third embodiment of the infusion port.
Figure 10:
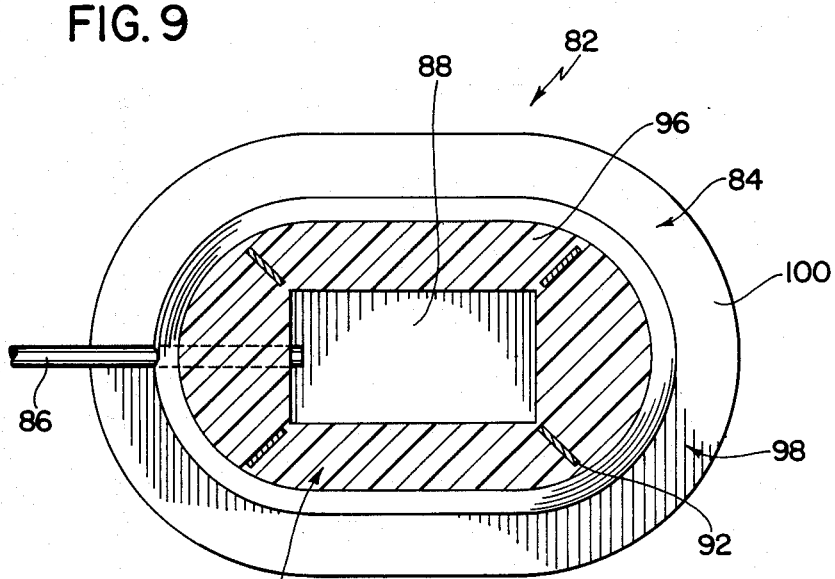
FIG. 10 is an enlarged sectional view taken along line 10—10 in FIG. 9.
Figure 11:
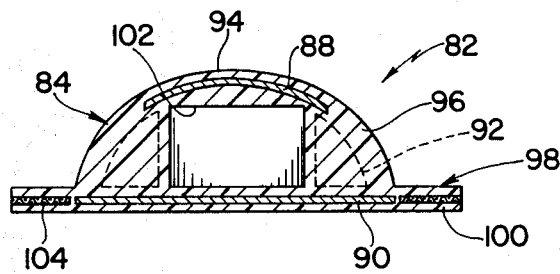
FIG. 11 is an enlarged sectional view taken along line 11—11 in FIG. 9.

A third embodiment of the infusion port of the instant invention is illustrated and generally indicated at 82 in FIGS. 9 through 11. The infusion port 82 is of elongated form and it is also generally similar in construction to the infusion port 28, and it comprises a septum generally indicated at 84 and a catheter element 86. The infusion port 82, however, further comprises a top needle shield 88, a bottom needle shield 90, and a plurality of side needle shields 92. The septum 84 is preferably integrally molded from a suitable nontoxic rubberized material, such as a silicone rubber, and it comprises a top wall portion 94, a side wall portion 96, and a base portion generally indicated at 98 having a peripheral rim 100. The top wall portion 94 and the side wall portion 96 cooperate to define a rounded oval dome-shaped element on the base portion 98; and they also cooperate with the base portion 98 for defining an interior cavity 102 in the septum 84. A reinforcing sheet 104 is embedded in the peripheral rim 100 of the base portion 98 for allowing the septum 84 to be more effectively sutured to tissue in a patient, and the catheter element 86 extends through the side wall portion 98 and into the interior cavity 102. The shields 88, 90 and 92 are preferably made of a corrosion-resistant metal, such as stainless steel, and they are provided for guiding the tip of a needle through the side wall portion 96 and into the cavity 102. The top guide plate 88 is of rounded, dome-shaped configuration, and it is positioned above the cavity 102; whereas the bottom shield 90 is of substantially planar configuration, and it is embedded in the base portion 98 beneath the cavity 102 and the side wall portions 96. The cavity 102 has a generally rectangular sectional configuration, and the shields 92 are embedded in the side wall portion 96 so that they extend outwardly from the corners of the cavity 102 as illustrated in FIG. 10.

For use and operation of the infusion port 82, it is installed in a patient in the manner hereinabove described with regard to the infusion port 28, and medication is introduced into the cavity 102 through the side wall portion 96. In this regard, if the tip of a needle which is inserted into the side wall portion 96 is directed toward the cavity 102, it will pass freely through the side wall portion 96 without contacting one of the guide plates 88, 90 or 92. If, however, the tip of the needle is misguided so that it would otherwise miss the cavity 102, it will contact one of the guide plates 88, 90 or 92 and be redirected toward the cavity 102. Generally, the infusion port 82 is similar in construction to the infusion port 28 and it has generally the same advantages with respect to its operation and construction as the infusion port 28. Further, it will be understood, however, that other embodiments of the infusion port of the instant invention wherein the top wall portion, the base portion and portions of the side wall portion are made entirely or partially of hardened plastic materials so that they act as needle shields for assuring that a needle tip passes into an internal cavity are also contemplated.

It is seen, therefore, that the instant invention provides a highly effective side entry infusion port which overcomes many of the disadvantages of the heretofore-available infusion ports. The infusion ports 28, 58 and 82 can all be effectively utilized for introducing medications into the bodies of patients. Further, they have substantially increased penetration areas so that they have substantially increased lifetimes as compared to the heretofore-available infusion ports. In addition, the skin penetration areas of patients in which they are implanted are also increased to allow adequate healing time for puncture wounds. Still further, because of the molded rubberized constructions of the infusion ports 28, 58 and 82, they are adapted to be worn substantially more comfortably than the heretofore available infusion ports. Hence, for these reasons, as well as the other reasons hereinabove set forth, it is seen that the infusion ports of the instant invention have significant advantages over the heretofore-available infusion ports and that they represent significant advancements in the art which have substantial merit from both medical and commercial standpoints.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An implantable infusion port for dispensing medication in the body of a patient comprising a septum having a base portion, a side wall portion and a top wall portion which cooperate to define an enclosed cavity in said septum, at least a portion of said side wall portion being made of a material which is penetrable by a hypodermic needle or the like for introducing medication into said cavity but which is substantially selfsealing upon removal of said needle therefrom, catheter means providing communication between said cavity and the exterior of said septum for dispensing said medication in the body of said patient, and impenetrable means within said port extending substantially upright relative to said base portion and operable for limiting the extent of penetration of said needle in said port in a direction substantially parallel to said base portion.

2. The implantable infusion port of claim 1 wherein said impenetrable means comprises a partition extending across said cavity.

3. The implantable infusion port of claim 2 wherein said partition is imperforate and joined to said base portion and top wall portion to provide a plurality of chambers isolated from one another, and a corresponding plurality of catheter lumens, one leading respectively from each of said chambers.

4. The implantable infusion port of claim 2 wherein said port is of elongated form and said partition extends in the lengthwise direction thereof, the elongated exterior sides of said port providing extended areas for penetration by said needle of said port from opposite sides thereof.

5. The implantable infusion port of claim 3 wherein said port is of elongated form and said partition extends in the lengthwise direction thereof, the elongated exterior sides of said port providing extended areas for penetration by said needle of said port from opposite sides thereof.

6. An implantable infusion port for dispensing medication in the body of a patient comprising a septum having a base portion, a side wall portion and a top wall portion which cooperate to define an enclosed cavity in said septum, at least a portion of said side wall portion being made of a material which is penetrable by a hypodermic needle or the like for introducing medication into said cavity but which is substantially self-sealing upon removal of said needle therefrom, catheter means providing communication between said cavity and the exterior of said septum for dispensing said medication in the body of said patient, and a partition in said septum separating said cavity into discrete first and second chambers, said catheter means including first and second catheter lumens which provide communication between said first and second chambers, respectively, and the exterior of said septum.

7. An implantable infusion port for dispensing medication in the body of a patient comprising a septum having a base portion, a side wall portion and a top wall portion which cooperate to define an enclosed cavity in said septum, at least a portion of said side wall portion being made of a material which is penetrable by a hypodermic needle or the like for introducing medication into said cavity but which is substantially self-sealing upon removal of said needle therefrom, catheter means providing communication between said cavity and the exterior of said septum for dispensing said medication in the body of said patient, guide means mounted in said septum for directing the tip of a needle inserted through said penetrable side wall portion into said cavity, and impenetrable means within said cavity extending substantially upright relative to said base portion and operable for limiting the extent of penetration of said needle tip in said port in a direction substantially parallel to said base portion.

8. The infusion port of claim 1 further comprising top and bottom needle shields.

* * * * *